(12) United States Patent
Emery et al.

(10) Patent No.: US 7,659,292 B2
(45) Date of Patent: Feb. 9, 2010

(54) FUNGICIDE COMPOSITIONS BASED ON PYRIDYLMETHYLBENZAMIDE AND PROPAMOCARB DERIVATIVE

(75) Inventors: Jane Catherine Emery, Essex (GB); Philip Eric Russell, Cambridge (GB); Richard Andrew Bardsley, Essex (GB); Jane Elizabeth Dancer, Cambridge (GB); Richard Mercer, Ecully (FR); David Stanley Holah, Cambridgeshire (GB)

(73) Assignee: Bayer Cropscience S.A. (FR)

( * ) Notice: Subject to any disclaimer, the term of this patent is extended or adjusted under 35 U.S.C. 154(b) by 270 days.

(21) Appl. No.: 10/471,125

(22) PCT Filed: Feb. 19, 2002

(86) PCT No.: PCT/FR02/00621

§ 371 (c)(1),
(2), (4) Date: Feb. 10, 2004

(87) PCT Pub. No.: WO02/069714

PCT Pub. Date: Sep. 12, 2002

(65) Prior Publication Data

US 2005/0176682 A1    Aug. 11, 2005

(30) Foreign Application Priority Data

Mar. 8, 2001    (FR) .................................. 01 03141

(51) Int. Cl.
A01N 43/40    (2006.01)
(52) U.S. Cl. ..................................... 514/357
(58) Field of Classification Search .................. 424/405
See application file for complete search history.

(56) References Cited

U.S. PATENT DOCUMENTS 6,503,933 B1 * 1/2003 Moloney et al. ............ 514/357
6,828,441 B2   12/2004 Moloney et al. ............ 546/296

FOREIGN PATENT DOCUMENTS

| EP | 0398072 | 5/1990 |
| EP | 0472996 | 8/1991 |
| EP | 0775696 | 5/1995 |
| WO | WO 99/42447 | 8/1999 |
| WO | 03079788 | 10/2003 |
| ZA | 6706747 | * 8/1968 |

OTHER PUBLICATIONS

British Crop Protection Council: The Pesticide Manual, 12$^{th}$ Edition, CDS Tomlin (ED), Farnham, GB XP002200421, pp. 410-411, 578, 578-580, 580-581, 632-633, 659, 669, 781-782, 962-963.

* cited by examiner

*Primary Examiner*—Alton N Pryor
(74) *Attorney, Agent, or Firm*—Ostrolenk Faber LLP

(57) ABSTRACT

1) Fungicidal compositions comprising:
   a) at least one pyridylmethylbenzamide derivative of formula (I):

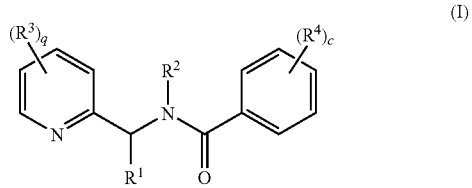

in which the various radicals are as defined in the description,
and
   b) at least one compound (II), which is propamocarb.

2) Method of curatively or preventively combating phytopathogenic fungi in crops, characterized in that an effective, nonphytotoxic amount of one of these fungicidal compositions is applied to the aerial parts of the plants.

12 Claims, No Drawings

FUNGICIDE COMPOSITIONS BASED ON PYRIDYLMETHYLBENZAMIDE AND PROPAMOCARB DERIVATIVE

CROSS REFERENCE TO RELATED APPLICATION

The present application is a 35 U.S.C. §371 national phase conversion of PCT/FR02/00621, filed Feb. 19, 2002, which claims priority of French Application No. 01/03141 filed Mar. 8, 2001.

The present invention relates to novel fungicidal compositions comprising at least one pyridylmethylbenzamide derivative and propamocarb or one of its salts and being intended in particular for crop protection. It likewise relates to a method of protecting crops against fungal disease by applying these compositions.

European patent application EP-A-1 056 723 in particular discloses compounds of the pyridylmethylbenzamide type which have a fungicidal action and allow prevention of the growth and development of phytopathogenic fungi which attack, or are likely to attack, crops.

Propamocarb, moreover, is a widely known fungicidal active substance which is sold in particular under the name Previcur®. Propamocarb, in the form of the salt with hydrochloric acid, is described for example in patents DE 1567169 and DE 1643040 and also in "The Pesticide Manual", a World Compendium, 11th edition, C. D. S. Tomlin, British Crop Protection Council, pages 1015-17, No. 599.

However, it is always desirable to improve the products which can be used by the farmer to combat fungal diseases in crops, and especially to combat downy mildews.

It is also always desirable to reduce the amounts of chemicals dispersed into the environment in order to combat fungal infestations in crops, particularly by reducing the rates at which the products are applied.

It is always desirable, finally, to increase the number of antifungal products available to the farmer, allowing him or her to select the product most suitable for the particular application.

One aim of the invention is therefore to provide a novel fungicidal composition which is of use in solving the problems set out above.

Another aim of the invention is to provide a novel fungicidal composition which is of use in the preventive and curative treatment of fungal diseases in crops such as, for example, solanums, cereals and grapevines.

Another aim of the invention is to provide a novel fungicidal composition exhibiting improved efficacy against downy mildew, powdery mildew, rust and botrytis in cereals, solanums and grapevines.

Another aim of the invention is to provide a novel fungicidal composition exhibiting improved efficacy against downy mildew and/or powdery mildew and/or botrytis in grapevines.

It has now been found that these aims can be achieved in whole or in part by virtue of the fungicidal compositions of the present invention.

The present invention therefore provides firstly fungicidal compositions comprising:

a) at least one pyridylmethylbenzamide derivative of formula (I)

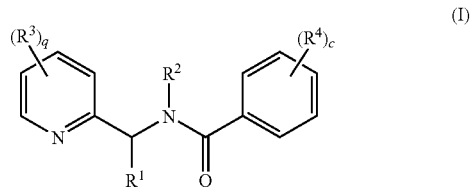

in which:

$R^1$ is selected from a hydrogen atom, an optionally substituted alkyl radical and an optionally substituted acyl radical;

$R^2$ is selected from a hydrogen atom and an optionally substituted alkyl radical;

$R^3$ and $R^4$, which are identical or different, are selected independently from a halogen atom, a hydroxyl radical, a cyano radical, a nitro radical, an —$SF_5$ radical, a trialkylsilyl radical, an optionally substituted amino radical, an acyl radical, and a group E, OE or SE in which E is selected from an alkyl, alkenyl, alkynyl, cycloalkyl, cycloalkenyl, aryl and heterocyclyl radical, each of which can be optionally substituted;

c represents 0, 1, 2, 3 or 4;

q represents 0, 1, 2, 3 or 4;

and their possible optical and/or geometric isomers, tautomers and addition salts with an acid or a base that are acceptable in the agricultural field;

and b) at least one compound (II), which is propamocarb.

In the definitions of the compounds of formula (I) set out above, the various radicals and chemical terms employed, unless specified otherwise, have the following meanings:

"alkyl" or "alkyl-" denotes a saturated linear or branched hydrocarbon radical containing from 1 to 6 carbon atoms;

"alkenyl" denotes a linear or branched hydrocarbon radical containing from 1 to 6 carbon atoms and an unsaturation in the form of a double bond;

"alkynyl" denotes a linear or branched hydrocarbon radical containing from 1 to 6 carbon atoms and an unsaturation in the form of a triple bond;

"alkoxy" denotes an alkyl-oxy radical;

"acyl" denotes the formyl radical or an alkoxycarbonyl radical;

"cycloalkyl" denotes a saturated cyclic hydrocarbon radical containing from 3 to 8 carbon atoms;

"aryl" denotes a phenyl or naphthyl radical;

"heterocyclyl" denotes an unsaturated or fully or partly saturated cyclic radical containing from 3 to 8 atoms selected from carbon, nitrogen, sulphur and oxygen nonlimiting examples including pyridyl, pyridinyl, quinolyl, furyl, thienyl, pyrrolyl and oxazolinyl;

the term "optionally substituted" signifies that the radicals thus qualified may be substituted by one or more radicals selected from chlorine, bromine, fluorine, iodine, alkyl, alkoxy, hydroxyl, nitro, amino; cyano and acyl.

The compounds of formula (I) are described for example in patent application EP-A-1 056 723 and preference among them will be given to the compounds possessing one of the following characteristics, taken individually or in combination:

$R^1$ and $R^2$, which are identical or different, are selected independently from a hydrogen atom and an optionally substituted alkyl radical;

$R^3$ and $R^4$, which are identical or different, are selected independently from a halogen atom, a hydroxyl radical, a nitro radical, an optionally substituted amino radical, an acyl radical, and a group E, OE or SE in which E is selected from an alkyl, cycloalkyl, phenyl and heterocyclyl radical, each of which can be optionally substituted;

c represents 0, 1, 2 or 3;

q represents 0, 1, 2 or 3;

and their possible optical and/or geometric isomers, tautomers and addition salts with an acid or a base that are acceptable in the agricultural field.

Among the compounds of formula (I) further preference will be given to the compounds possessing the following characteristics, taken individually or in combination:

$R^1$ and $R^2$, which are identical or different, are selected independently from a hydrogen atom and a methyl or ethyl radical;

$R^3$ and $R^4$, which are identical or different, are selected independently from a halogen atom, a nitro radical, an optionally substituted amino radical and an alkyl, cycloalkyl, phenyl or heterocyclyl radical, each of which can be optionally substituted;

c represents 1 or 2;

q represents 1 or 2;

and their possible optical and/or geometric isomers, tautomers and addition salts with an acid or a base that are acceptable in the agricultural field.

More particularly, the compounds of formula (I) possess the following characteristics:

$R^1$ and $R^2$ each represent a hydrogen atom;

$R^3$ and $R^4$, which are identical or different, are selected independently from a halogen atom, a nitro radical, an alkyl radical and a trifluoromethyl radical;

c and q represent, independently of one another, 2;

and their possible tautomers and addition salts with an acid or a base that are acceptable in the agricultural field.

By way of example, the following compounds of formula (I) are very particularly preferred within the context of the present invention:

Compound (Ia): 2,6-dichloro-N-{[3-chloro-5-(trifluoromethyl)-2-pyridinyl]methyl}benzamide;

Compound (Ib): N-{[3-chloro-5-(trifluoromethyl)-2-pyridinyl]methyl}-2-fluoro-6-nitrobenzamide;

Compound (Ic): N-{[3-chloro-5-(trifluoromethyl)-2-pyridinyl]methyl}-2-methyl-6-nitrobenzamide;

and their possible tautomers and addition salts with an acid or a base that are acceptable in the agricultural field.

The compound (II) defined above is probamocarb, namely propyl 3-(dimethylamino)propylcarbamate, which is described for example in "The Pesticide Manual", 11th edition, C D S Tomlin, British Crop Protection Council, pages 1015-1017, No. 599. Advantageously, the propamocarb used in the compositions of the present invention will be in the form of the hydrochloride, i.e. the addition salt of propamocarb with hydrochloric acid, known commercially under the name Previcur®.

The propamocarb which is useful for the compositions of the present invention can also be used in the form of the salt with fosetyl, as described in patent application EP-A-1 056 755 or else in patent application WO-A-98/44801.

Advantageously, the compositions of the present invention comprise compound (Ia) or compound (Ib) or compound (Ic) with compound (II). The preferred compositions of the present invention comprise compound (Ia) with compound (II).

The present invention accordingly provides fungicidal compositions comprising at least one pyridylmethylbenzamide derivative of formula (I) as defined above and at least one compound (II) as defined above, the compound (I)/compound (II) ratio being between 1/500 and 1/1, preferably between 1/200 and 1/5, more preferably between 1/150 and 1/10.

The compound (I)/compound (II) ratio is defined as being the ratio by weight of these two compounds. The same is true of any ratio of two chemical compounds mentioned subsequently in the present text, unless a different definition of this ratio is expressly indicated.

It will be appreciated that the said fungicidal compositions may comprise a single compound (I) or more than one such compound and/or a single compound (II) or more than one such compound, and also one or more other fungicidal, herbicidal, insecticidal and/or plant growth regulator compounds, depending on the use for which the said compositions are intended.

Accordingly, the fungicidal compositions of the present invention may further comprise, for example, one or more other active fungicidal substances selected from acibenzolar-S-methyl, azoxystrobin, benalaxyl, benomyl, blasticidin-S, bromuconazole, captafol, captan, carbendazim, carboxin, carpropamid, chlorothalonil, fungicidal compositions based on copper, copper derivatives such as copper hydroxide and copper oxychloride, cyazofamid, cymoxanil, cyproconazole, cyprodinyl, dichloran, diclocymet, diethofencarb, difenoconazole, diflumetorim, dimethomorph, diniconazole, discostrobin, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferimzone, fluazinam, fludioxonil, flumetover, fluquinconazole, flusilazole, flusulfamide, flutolanil, flutriafol, folpel, furalaxyl, furametpyr, guazatine, hexaconazole, hymexazol, imizalil, iprobenphos, iprodione, isoprothiolane, kasugamycin, kresoxim-methyl, mancozeb, maneb, mefenoxam, mepanipyrim, metalaxyl and its enantiomeric forms such as metalaxyl-M, metconazole, metiram-zinc, metominostrobin, oxadixyl, pefurazoate, penconazole, pencycuron, phosphorous acid and its derivatives such as fosetyl-Al, phthalide, picoxystrobin, probenazole, prochloraz, procymidone, propiconazole, pyraclostrobin, pyrimethanil, pyroquilon, quinoxyfen, silthiofam, simeconazole, spiroxamine, tebuconazole, tetraconazole, thiabendazole, thifluzamide, thiophanate, for example thiophanate-methyl, thiram, triadimefon, triadimenol, tricyclazole, tridemorph, trifloxystrobin, triticonazole, valinamide derivatives such as, for example, iprovalicarb, vinclozolin, zineb and zoxamide.

The invention further provides a method of curatively or preventively combating phytopathogenic fungi in crops, characterized in that an (agronomically) effective and non-phytotoxic amount of a fungicidal composition of the invention is applied to the soil in which the plants are growing or are liable to grow, to the leaves and/or the fruits of the plants or to the seeds of the plants.

The compositions of the invention are advantageous for combating fungal diseases in numerous crops such as, for example, cereals, vegetables, solanums, market-garden crops, grapevines, fruits in general, and especially for combating downy mildew, damping off, septoria disease and *Pythium* sp. in these crops.

The compositions of the invention may also be used for combating other phytopathogenic diseases in crops that are well known to the person skilled in the art to whom the compounds of formula (I) and the compounds (II) are available.

These compounds generally improve markedly the respective isolated actions of compound (I) and of compound (II) for a certain number of fungi which are particularly harmful in crops, particularly for solanums (tomatoes, potatoes, etc.), more particularly for downy mildew in potatoes and downy mildew in tomatoes, while preserving an absence of phytotoxicity with regard to these crops. There is therefore an improvement in the spectrum of activity and a possibility of reducing the respective dose of each active substance used, the latter quality being particularly important for ecological reasons which are easy to comprehend.

In the compositions of the invention, the compound (I)/compound (II) ratio is advantageously selected so as to produce a synergistic effect. The term "synergistic effect" refers in particular to the effect defined by S. R. Colby in an article titled "Calculating synergistic and antagonistic responses of herbicide combinations", *Weeds*, (1967), 15, pages 20-22.

The latter article makes use of the formula:

$$E = X + Y - \frac{XY}{100}$$

in which E represents the expected percentage inhibition of the disease for the combination of the two fungicides at defined doses (for example equal respectively to x and y), X is the observed percentage inhibition of the disease by compound (I) at a defined dose (equal to x), Y is the observed percentage inhibition of the disease by compound (II) at a defined dose (equal to y). When the observed percentage inhibition of the combination is greater than E, there is a synergistic effect.

A synergistic effect is also understood to be that defined by applying the method of Tammes, "Isoboles, a graphic representation of synergism in pesticides", *Netherlands Journal of Plant Pathology*, 70, (1964), pages 73-80.

The abovementioned ranges for the compound (I)/compound (II) ratio are by no means limitative of the scope of the invention but rather are cited by way of indication, it being well within the abilities of the person skilled in the art to carry out complementary tests in order to find other values for the dosage ratio of these two compounds at which a synergistic effect is observed.

Accordingly, the compositions of the invention comprising compound (I) and compound (II) allow quite remarkable synergistic properties to be observed.

According to one variant of the compositions of the invention, the compound (I)/compound (II) ratio is advantageously between 1/200 and 1/5, preferably between 1/140 and 1/10.

The invention therefore also comprises methods of treating plants to counter phytopathogenic diseases, characterized in that a composition comprising at least one compound of formula (I) with at least one compound (II) is applied. It is also possible to apply a composition comprising both active substances or else two compositions each comprising one of the two active substances, either simultaneously or in succession so as to have the conjoint effect.

These compositions embrace not only compositions which are ready to be applied to the crop to be treated by means of an appropriate device, such as a sprayer, but also commercial concentrated compositions which have to be diluted before application to the crop.

The present invention provides a method of combating a wide variety of phytopathogenic diseases in crops, particularly for combating septoria disease and downy mildew. These diseases can be combated by direct foliar application.

The present invention therefore provides a method of curatively or preventively combating phytopathogenic diseases in crops which comprises treating the said crop (for example by application or by administration) with an effective, nonphytotoxic amount of a combination as defined above. By treatment of the crop is meant application or administration of a fungicidal composition as described above to the aerial parts of the crops or to the soil in which they are growing, which are infested or liable to be infested by a phytopathogenic disease, such as downy mildew or septoria disease, for example. By treatment of the crop is also meant the treatment of reproduction products of the crop, such as seeds or tubers for example.

The compositions described below are generally used for application to growing plants or to loci on which crops are grown, or for the dressing or coating of seeds.

Among the means which are suitable for applying the compositions of the invention mention may be made of the use of powders, foliar sprays, granules, mists or foams, or else means in the form of suspensions of finely divided or encapsulated compositions; for the treatment of soils or roots with liquid imbibitions, powders, granules, fumes or foams; for application to the seeds of plants, the use, as seed dressing or seed coating agents, of powders or of liquid slurries.

The compositions of the invention are, appropriately, applied to the vegetation and in particular to the leaves infested with the phytopathogenic fungi. Another method of applying the compounds or compositions of the invention is to add a formulation comprising the active substances to the irrigation water. This irrigation may be an irrigation using sprinklers.

The formulations which are suitable for applying the compositions of the invention comprise formulations suitable for use in the form, for example, of sprays, powders, granules, mists, foams, emulsions or others.

In practice, for combating phytopathogenic diseases in crops, one method, for example, consists in applying an effective amount of a composition of the invention to the plants or to the medium in which they are growing. For a method of this kind, the active substances are generally applied to the locus itself in which the infestation is to be controlled, the said application taking place at an effective dose of between approximately 1 g and approximately 1 000 g of active substances in total per hectare of locus treated. Under ideal conditions, depending on the nature of the phytopathogenic fungus to be treated, a lower dose may provide adequate protection. Conversely, under poor climatic conditions, resistance or other factors may require higher doses of active substance.

The effective working doses of the combinations employed in the invention may vary within wide proportions, according in particular to the nature of the phytopathogenic fungi to be eliminated or the degree of infestation, for example, of the plants by these fungi.

The optimum dose commonly depends on a number of factors, for example on the type of phytopathogenic fungus to be treated, on the type or level of development of the infested plant, on the density of vegetation, or else on the method of application. More preferably, an effective dose of active substances (I) and (II) is between approximately 5 g/ha and approximately 700 g/ha.

For their use in practice, the compositions of the invention can be used alone and may also advantageously be used in formulations comprising one or other of the active substances or else both together, in association or combination with one or more other, compatible components which are, for example, solid or liquid fillers or diluents, adjuvants, surfactants, or equivalents which are appropriate for the desired use and acceptable for agricultural uses. The formulations may be of any type which is known in the sector and suitable for application in all types of plantings or crops. These formulations, which can be prepared in any manner known in this sector, also form part of the invention.

The formulations may also comprise other types of ingredients such as protective colloids, adhesives, thickeners, thixotropic agents, penetrants, oils for spraying, stabilizers, preservatives (especially antimould agents), sequestrants, or others, and other active ingredients which are known to possess pesticidal properties (especially fungicidal, insecticidal, acaricidal or nematicidal properties) or to possess plant growth regulator properties. More generally, the compounds used in the invention may be combined with any solid or liquid additives which correspond to the normal formulation techniques.

In general, the formulations of the invention commonly contain from approximately 0.05% to approximately 99% (by weight) of one or more compositions of the invention, from approximately 1% to approximately 95% of one or more solid or liquid fillers, and optionally from approximately 0.1% to approximately 50% of one or more other, compatible compounds, such as surfactants or others.

In the present specification, the term "filler" signifies an organic or inorganic, natural or synthetic component with which the active components are combined in order to facilitate their application to, for example, the plants, seeds, or soil. Consequently, this filler is generally inert and it must be acceptable (for example, acceptable for agronomic use, especially for treating plants).

The filler can be solid, examples being clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina, or silicates, especially aluminium silicates or magnesium silicates. Solid fillers which are suitable for granules are as follows: natural rocks, crushed or broken, such as calcite, marble, pumice, sepiolite and dolomite; synthetic granules of organic or inorganic flours; granules of organic material such as sawdust, coconut shell, corn ear or corn husk or tobacco stem; kieselguhr, tricalcium phosphate, powdered cork, or adsorbent carbon black; water-soluble polymers, resins, waxes; or solid fertilizers. If desired, such compositions may comprise one or more compatible agents such as wetting agents, dispersants, emulsifiers or colorants which, when solid, may also serve as diluents.

The fillers may also be liquid, examples including the following: water, alcohols, especially butanol or glycol, and their ethers or esters, especially methyl glycol acetate; ketones, especially acetone, cyclohexanone, methyl ethyl ketone, methyl isobutyl ketone or isophorone; petroleum fractions such as paraffinic or aromatic hydrocarbons, especially xylenes or alkylnaphthalenes; mineral oils or plant oils; chlorinated aliphatic hydrocarbons, especially trichloroethane or methylene chloride; chlorinated aromatic hydrocarbons, especially chlorobenzenes; water-soluble or highly polar solvents such as dimethylformamide, dimethyl sulphoxide, N,N-dimethylacetamide and N-methylpyrrolidone; N-octylpyrrolidone, liquefied gases; or others, either separately or in a mixture.

The surfactant may be an emulsifier, a dispersant or a wetting agent, of ionic or nonionic type, or a mixture of these surfactants. Among them use is made, for example, of salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (especially alkylphenols or arylphenols), ester salts of sulphosuccinic acid, taurine derivatives (especially alkyl taurates), phosphoric esters of alcohols or of polycondensates of ethylene oxide with phenols, esters of fatty acids with polyols, or sulphate, sulphonate or phosphate functional derivatives of the above-described compounds. The presence of at least one surfactant is generally essential when the active substances and/or the inert filler are only sparingly soluble or insoluble in water and when the filler of the said composition to be applied is water.

The formulations of the invention may further comprise other additives such as adhesives or colorants. Adhesives such as carboxymethylcellulose, or synthetic or natural polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be used in the formulations. It is possible to use colorants such as inorganic pigments, such as the following, for example: iron oxides, titanium oxides, or Prussian blue; organic dyes, such as those of the alizarin, azo or metal phthalocyanine type; or trace elements such as salts of iron, manganese, boron, copper, cobalt, molybdenum or zinc.

The formulations comprising the compositions of the invention that are employed for combating phytopathogenic fungi in crops may also comprise stabilizers, other fungicidal agents, insecticides, acaricides, nematicides, anthelmintics or anticoccidials, bactericides, attractants or repellents or pheromones for arthropods or vertebrates, deodorizers, flavourings or colorants.

These substances may be selected purposely for improving the intensity, persistence, safety or spectrum of action on the phytopathogenic fungi in the crops or for rendering the composition capable of accomplishing other useful functions for the treated surfaces.

For their use in agriculture, the compositions of the invention are accordingly formulated in various liquid or solid forms.

As solid formulations, mention may be made of powders for dusting (with an active substance content which can be up to 100%) and granules, especially those obtained by extrusion, spraying, compacting, impregnation of a granulated support, or granulation from a powder (the active substance content of these granules being between 0.5 and 80% in the latter cases).

The fungicidal compositions of the invention may also be used in the form of powders for dusting; it is also possible to use formulations comprising 50 g of active substances and 950 g of talc; it is also possible to use formulations containing 20 g of active substances, 10 g of finely divided silica and 970 g of talc; these constituents are mixed and ground and the mixture is applied by dusting.

As formulations which are liquid or which are intended to constitute liquid compositions at the time of application, mention may be made of solutions, especially water-soluble concentrates, emulsifiable concentrates, emulsions, concentrated suspensions and wettable powders (or sprayable powder).

The concentrated suspensions which can be applied by spraying are prepared so as to obtain a stable fluid product which does not settle and which leads to effective bioavailability of the active substances. These suspensions commonly contain from 5% to 75% of active substances, preferably from 10% to 25%, from 0.5 to 75% of surfactants, preferably from 5% to 50%, from 0 to 10% of appropriate additives, such as thickeners which are mineral or organic in origin, antifoams, corrosion inhibitors, adhesives, preservatives, such as Proxel GXL® for example, antifreezes and, as vehicle, water or an organic liquid in which the active substances are sparingly soluble or insoluble: certain organic solids or mineral salts may be dissolved in the vehicle in order to help prevent sedimentation or as antifreezes for the water. In certain cases, and especially for formulations intended for treating seeds, one or more colorants may be added.

For foliar application, the choice of surfactants is essential in order to ensure effective bioavailability of the active substances; accordingly, use will be made preferably of a combination of a hydrophilic-type surfactant (HLB>10) and of a lipophilic-type surfactant (HLB<5). Such combinations of surfactants are described for example in the as-yet unpublished French patent application No. 00 04015.

By way of example, here are 3 possible formulations of the suspension concentrate type, adapted for different crops:

EXAMPLE SC 1 (in g/kg)

This example is more suitable for monocotyledonous crops (cereals, rice, etc.)

| | |
|---|---|
| active substances | 150 |
| hydrophilic-type surfactant (for example Rhodasurf 860P) | 300 |
| lipophilic-type surfactant (for example Plurafac LF 700) | 150 |
| ethoxylated tristyrylphenol phosphate | 50 |
| antifoam | 5 |
| propylene glycol | 30 |
| Aerosil 200 | 20 |
| Attagel 50 | 40 |
| water (qs 1 kg) | 255 |

EXAMPLE SC2 (in g/kg)

This example is more suitable for dicotyledonous crops (grapevines, fruit trees, etc.)

| | |
|---|---|
| active substances | 150 |
| hydrophilic-type surfactant (for example Rhodasurf 860P) | 150 |
| ethoxylated tristyrylphenol phosphate | 50 |
| antifoam | 5 |
| propylene glycol | 30 |
| Aerosil 200 | 20 |
| Attagel 50 | 40 |
| water (qs 1 kg) | 555 |

EXAMPLE SC3 (in g/kg)

This example is more specifically adapted to the treatment of seeds.

| | |
|---|---|
| active substances | 50 |
| hydrophilic-type surfactant (for example Rhodasurf 860P) | 5 |
| ethoxylated tristyrylphenol phosphate | 15 |
| antifoam | 1 |
| propylene glycol | 30 |
| colorant | 20 |
| Rhodopol G | 1.5 |
| Proxel GXL | 1.5 |
| water (qs 1 kg) | 876 |

These formulations will preferably be produced using the following technique:

The selected surfactants (hydrophilic-type surfactant+lipophilic-type surfactant+ethoxylated tristyrylphenol phosphate) are mixed into the required amount of water using a turbine mixer; following homogenization, the other constituents of the formula apart from the active substances are then mixed in.

Then the active substances are added and, optionally, the thickener of mineral origin (Aerosil 200 and Attagel 50) in order to obtain a mixture with a viscous consistency. The resulting mixture is then ground using a high-speed turbo mixer mill and then a ball mill so as to give a D50 of the order of from 1 to 3 μm and a D90 of between 3 and 8 μm.

Where no thickener of mineral origin is used, the thickener of natural origin (Rhodopol G) is added next and the mixture is stirred until an appropriate viscosity is obtained.

The wettable (or sprayable) powders are commonly prepared such that they contain from 20% to 95% of active substances, and they commonly contain, in addition to the solid vehicle, from 0% to 30% of a wetting agent, from 3% to 20% of a dispersant, and, when necessary, from 0.1% to 10% of one or more stabilizers and/or other additives, such as penetrants, adhesives, or anticaking agents, colorants, etc.

In order to obtain the sprayable or wettable powders, the active substances are intimately mixed in appropriate mixers with the additional substances and are ground using mills or other appropriate grinders. Sprayable powders are obtained whose wettability and suspension characteristics are advantageous; they can be suspended with water at any desired concentration, and these suspensions can be used very advantageously in particular for application, for example, to the leaves of plants or to seeds.

By way of example, here are various compositions of wettable powders (or sprayable powders):

EXAMPLE WP 1

| | |
|---|---|
| active substances | 50% |
| ethoxylated fatty alcohol (wetting agent) | 2.5% |
| ethoxylated phenylethylphenol (dispersant) | 5% |
| chalk (inert vehicle) | 42.5% |

EXAMPLE WP 2

| | |
|---|---|
| active substances | 10% |
| synthetic C13 oxo alcohol of branched type, ethoxylated with 8 to 10 ethylene oxide units (wetting agent) | 0.75% |
| neutral calcium lignosulphonate (dispersant) | 12% |
| calcium carbonate (inert filler) | qs 100% |

EXAMPLE WP 3

This wettable powder contains the same ingredients as in the preceding example, in the following proportions:

| | |
|---|---|
| active substances | 75% |
| wetting agent | 1.50% |
| dispersant | 8% |
| calcium carbonate (inert filler) | qs 100% |

EXAMPLE WP 4

| | |
|---|---|
| active substances | 90% |
| ethoxylated fatty alcohol (wetting agent) | 4% |
| ethoxylated phenylethylphenol (dispersant) | 6% |

EXAMPLE WP 5

| | |
|---|---|
| active substances | 50% |
| mixture of anionic and nonionic surfactants (wetting agent) | 2.5% |
| sodium lignosulphonate (dispersant) | 5% |
| kaolinic clay (inert vehicle) | 42.5% |

The aqueous emulsions and dispersions, for example the compositions obtained by diluting a wettable powder of the invention with water, are included within the general scope of the present invention. The emulsions may be of the water-in-oil or oil-in-water type and they may have a thick consistency like that of a mayonnaise sauce.

The fungicidal compositions of the invention may be formulated in the form of water-dispersible granules which are likewise included within the scope of the invention. These dispersible granules, with an apparent density which is generally between approximately 0.3 and 0.6, have a particle size which is generally between approximately 150 and 2 000 and preferably between 300 and 1 500 microns.

The active substance content of these granules is generally between approximately 1% and 90%, and preferably between 25% and 90%. The remainder of the granules is composed essentially of a solid filler and, optionally, of surfactant adjuvants which impart water-dispersibility properties to the granules. These granules may be essentially of two distinct types depending on whether the filler used is soluble or insoluble in water. When the filler is water-soluble, it may be mineral or, preferably, organic. Excellent results have been obtained with urea. In the case where the filler is insoluble it is preferably mineral, such as for example kaolin or bentonite. In that case it is advantageously accompanied by surfactants (in a proportion of from 2 to 20% by weight of the granules) of which more than half is composed, for example, of at least one, essentially anionic dispersant, such as an alkali metal or alkaline earth metal polynaphthalenesulphonate or an alkali metal or alkaline earth metal lignosulphonate, the remainder consisting of nonionic or anionic wetting agents such as an alkali or alkaline earth metal alkylnaphthalenesulphonate. Furthermore, although not indispensable, it is possible to add other adjuvants such as antifoams.

The granules may be prepared by mixing the required ingredients then granulating the mixture by a number of techniques which are known per se (granulator, fluid bed, atomizer, extrusion, etc.). The final procedure is normally a crushing operation followed by screening to the particle size selected within the abovementioned limits. It is also possible to use granules obtained as before then impregnated with a composition comprising the active substances.

The granules are preferably obtained by extrusion, operating as indicated in the examples below.

EXAMPLE DG1

Dispersible Granules

90% by weight of active substances and 10% of urea pellets are mixed in a mixer. The mixture is subsequently ground in a toothed roll crusher. A powder is obtained which is wetted with approximately 8% by weight of water. The moist powder is extruded in a perforated-roll extruder. This gives granules which are dried and then crushed and screened, so as to retain only those granules with a size of between 150 and 2 000 microns.

EXAMPLE DG2

Dispersible Granules

The following constituents are mixed in a mixer:

| | |
|---|---|
| active substances | 75% |
| wetting agent (sodium alkylnaphthalene sulphonate) | 2% |
| dispersant (sodium polynaphthalenesulphonate) | 8% |
| water-insoluble inert filler (kaolin) | 15% |

This mixture is granulated in a fluid bed in the presence of water and then dried, crushed and screened to give granules with a size of between 0.15 and 0.80 mm.

These granules may be used alone or in solution or dispersion in water in such a way as to give the desired dose. They may also be used for preparing compositions with other active substances, especially fungicides, the latter being in the form of wettable powders or granules or aqueous suspensions.

The fungicidal compositions of the invention commonly contain from 0.5 to 95% of the association of compound (I) and compound (II). The composition in question may be a concentrated composition, i.e. the commercial product combining compound (I) and compound (II). It may also be a dilute composition which is ready to be applied to the crops to be treated. In the latter case, dilution with water can be carried out either starting from a concentrated commercial composition containing compound (I) and compound (II) (this mixture is called a ready mix) or by means of mixing at the time of use (in this case, the mixture is referred to as a tank mix) two concentrated commercial compositions each containing compound (I) and compound (II).

The invention lastly provides a method of curatively or preventively combating phytopathogenic fungi in crops, characterized in that an effective, nonphytotoxic amount of a fungicidal composition of the invention is applied to the plants to be treated.

The phytopathogenic fungi in crops that can be combated by this method are, in particular those:
    from the group of the oomycetes:

of the genus *Phytophthora* such as *Phytophthora infestans* (solanum late blight, particularly potato or tomato blight), of the family of the Peronosporaceae, especially *Plasmopara viticola* (grapevine downy mildew), *Plasmopara halstedii* (sunflower downy mildew), *Pseudoperonospora* sp. (in particular, cucurbit downy mildew and hop downy mildew), *Bremia lactucae* (lettuce downy mildew), *Peronospora tabacinae* (tobacco downy mildew), *Peronospora parasitica* (cabbage downy mildew), *Peronospora viciae* (pea downy mildew), and *Peronospora destructor* (onion downy mildew);

from the group of the adelomycetes:

of the genus *Alternaria*, for example *Alternaria solani* (solanium early blight, and especially early blight in tomatoes and potatoes), of the genus *Guignardia*, especially *Guignardia bidwelli* (grapevine black rot), of the genus *Oidium*, for example grapevine powdery mildew (*Uncinula necator*), powdery mildew of leguminous crops, for example *Erysiphe polygoni* (crucifer powdery mildew), *Leveillula taurica*, *Erysiphe cichoracearum*, *Sphaerotheca fuligena* (powdery mildew in cucurbits, composites and tomatoes), *Erysiphe communis* (powdery mildew in beet and cabbage), *Erysiphe pisi* (powder mildew in peas and alfalfa), *Erysiphe polyphaga* (powdery mildew in beans and cucumber), *Erysiphe umbelliferarum* (powdery mildew in umbellifers, especially carrots), *Sphaerotheca humuli* (hop powdery mildew);

from the group of soil fungi:

of the genus *Pythium* sp., of the genus *Aphanomyces* sp., especially *Aphanomyces euteiches* (white root rot in peas), *Aphanomyces cochlioides* (root rot in beet).

The term "is/are applied to the plants to be treated" is intended to signify, in the sense of the present text, that the fungicidal compositions that are subjects of the invention may be applied by means of various treatment techniques such as:

the spraying of a liquid comprising one of the said compositions onto the aerial parts of the said plants, dusting, incorporation of granules or powders into the soil, irrigation around the said plants, and, in the case of trees, injection or painting on, the dressing or coating of seeds of the said plants by means of a slurry comprising one of the said compositions.

The spraying of a liquid onto the aerial parts of the crops to be treated is the preferred treatment method.

The examples which follow are given purely by way of illustration of the invention, and do not impose any limitation whatsoever thereon.

Although the invention has been described in terms of numerous preferred variants, the person skilled in the art will appreciate that many modifications, substitutions, omissions and changes can be made without departing from the spirit of this invention. It is thus clearly understood that the scope of the present invention is limited solely by the scope of the claims which follow, and by their equivalents.

EXAMPLE

Test of a Composition Against Late Blight in Potatoes (*Phytophthora infestans*: Preventive Action)

The following active substances are used for this test:

compound (Ia) in the form of a suspension concentrate (10 SC)

compound (II): propamocarb hydrochloride (Previcur-N®, in the form of a soluble concentrate (66.5 SL).

Potato plants (three weeks old) are treated by automatic spraying (Mardrive) at a rate of 200 l/ha. Six identical tests are carried out. Compounds (Ia) and (II) are mixed (tank mix) in different proportions which in the results table are expressed in g/ha.

All of the plants are inoculated 24 hours after treatment with a suspension of sporangia of *Phytophthora infestans*, containing 20 000 spores per ml.

The inoculated plants are covered for 2 days and then placed in a controlled atmosphere at 20° C. until the results are read off.

The degree of infestation is evaluated by rating on a scale ranging from 1 to 10, the value 0 denoting the absence of disease and the value 100 denoting complete infestation (100%).

For each treatment, the percentage disease control is calculated relative to untreated plants, and the theoretical results are calculated using the Colby formula described above.

The difference between the experimental results and the calculated results allows the degree of synergism between the two compounds to be determined.

The results are shown in the table below:

Test on Compound (Ia) and Compound (II)

Test on compound (Ia) and compound (II):

| | Concentration (g/ha) | Rating | Efficacy (obs.)/ % | Efficacy (exp.)/ % | Synergism (Colby) |
|---|---|---|---|---|---|
| Compound (Ia) | 5 | 4.3 | 48 | | — |
| | 25 | 3.3 | 60 | | — |
| Compound (II) | 400 | 8.3 | 0 | | — |
| | 600 | 6.8 | 18 | | — |
| (Ia) + (II) 1/80 | 5 + 400 | 2.8 | 66 | 48 | 18 |
| (Ia) + (II) 1/120 | 5 + 600 | 2.2 | 74 | 57 | 17 |
| (Ia) + (II) 1/16 | 25 + 400 | 1.5 | 82 | 60 | 22 |
| (Ia) + (II) 1/24 | 25 + 600 | 1.0 | 88 | 67 | 21 |

Untreated control: rating 8.3

The compositions of the invention comprising compound (Ia) and compound (II) exhibit a high level of synergism irrespective of the doses of each of the active substances and irrespective of the proportions of compound (Ia) to compound (II).

The invention claimed is:

1. A synergistic fungicidal compositions comprising:
   a) at least one pyridylmethylbenzamide derivative selected from the group consisting of 2,6-dichloro-N-{[3-chloro-5-(trifluoromethyl)-2-pyridinyl]methyl}benzamide, N-{[3-chloro-5-(trifluoromethyl)-2-pyridinyl]methyl}-2-fluoro-6-nitrobenzamide, and N-{[3-chloro-5-(trifluoromethyl)-2-pyridinyl]methyl}-2-methyl-6-nitrobenzamide and their possible optical and/or geometric isomers, tautomers and addition salts with an acid or a base that are acceptable in the agricultural field; and
   b) a compound (II), which is propamocarb;
wherein the compound (I)/compound (II) weight ratio is between 1/140 and 1/10.

2. The fungicidal composition of claim 1 wherein the pyridylmethylbenzamide derivative is 2,6-dichloro-N{[3-chloro-5-(trifluoromethyl)-2-pyridinyl]methyl}benzamide.

3. The fungicidal composition of claim 1 further comprising an agriculturally suitable inert vehicle and optionally an agriculturally suitable surfactant.

4. The fungicidal composition of claim 1 wherein said composition comprises from 0.5 to 99% of the combination of the pyridylmethylbenzamide derivative(s) and the propamocarb.

5. A method of combating phytopathogenic fungi in crops comprising applying an agronomically effective, nonphytotoxic amount of the fungicidal composition of claim 1 to soil in which the crops are growing or are liable to grow, to leaves and/or the fruits of the crops or to the seeds of the crops.

6. The method of claim 5 wherein the fungicidal composition is applied by spraying a liquid onto aerial parts of the crops to be treated.

7. The method of claim 5 wherein the amount of fungicidal composition corresponds to a dose of the pyridylmethylbenzamide derivative(s) and the propamocarb between approximately 1 g/ha and approximately 1 000 g/ha.

8. The method of claim 5 wherein the treated crop is selected from the group consisting of tomato, potato and grapevine.

9. The method of claim 6 wherein amount of fungicidal composition corresponds to a dose of the pyridylmethylbenzamide derivative(s) and propamocarb between approximately 1 g/ha and approximately 1 000 g/ha.

10. The method of claim 8 wherein phytopathogenic fungus combated is downy mildew in tomatoes, potatoes and grapevines.

11. A product comprising
  (A) at least one pyridylmethylbenzamide derivative selected from the group consisting of 2,6-dichloro-N-{[3-chloro-5-(trifluoromethyl)-2-pyridinyl]methyl}benzamide and N-{[3-chloro-5-(trifluoromethyl)-2-pyridinyl]methyl}-2-methyl-6-nitrobenzamide; and
  (B) propamocarb;
as a combined preparation for simultaneous, separate or sequential use in combating phytopathogenic fungi in crops in one locus;
wherein weight ratio is of (A) to (B) is between 1/140 and 1/10.

12. A fungicidal composition comprising:
  (A) at least one pyridylmethylbenzamide derivative selected from the group consisting of 2,6-dichloro-N-{[3-chloro-5-(trifluoromethyl)-2-pyridinyl]methyl}benzamide and N-{[3-chloro-5-(trifluoromethyl)-2-pyridinyl]methyl}-2-methyl-6-nitrobenzamide; and
  (B) propamocarb;
wherein weight ratio is of (A) to (B) is between 1/140 and 1/10.

* * * * *

UNITED STATES PATENT AND TRADEMARK OFFICE
CERTIFICATE OF CORRECTION

PATENT NO. : 7,659,292 B2
APPLICATION NO. : 10/471125
DATED : February 9, 2010
INVENTOR(S) : Emery et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this

Thirtieth Day of November, 2010

David J. Kappos
*Director of the United States Patent and Trademark Office*